United States Patent [19]

Kim et al.

[11] 4,126,642

[45] Nov. 21, 1978

[54] CONVERSION OF BUTADIENE (1,3) AND METHANOL

[75] Inventors: Leo Kim; Milton M. Wald, both of Houston, Tex.

[73] Assignee: Shell Oil Company, Houston, Tex.

[21] Appl. No.: 850,874

[22] Filed: Nov. 14, 1977

[51] Int. Cl.$^2$ .................. C07C 15/02; C10G 9/04
[52] U.S. Cl. .................. 260/673; 252/441; 260/666 B; 260/668 R; 260/676 R; 260/680 B; 260/683.47
[58] Field of Search ............ 260/673, 676 R, 666 B, 260/682, 680 B, 668 R, 691 R, 683.47

[56] References Cited

U.S. PATENT DOCUMENTS

| | | | |
|---|---|---|---|
| 2,456,584 | 12/1948 | Gorin et al. | 260/668 R |
| 2,492,984 | 1/1950 | Gross et al. | 260/676 R |
| 4,059,646 | 11/1977 | Wald et al. | 260/676 R |
| 4,059,647 | 11/1977 | Wald et al. | 260/676 R |

OTHER PUBLICATIONS

Ansinger "Mono-Olefins, Chemistry & Technology" 1968 Pergamon Press: p. 736, triptene, triptane.
A. Shaddan & P. W. Flanagan "Alkylation with α, Omega Dienes" ACS Div. Pet. Chem. Preprint 15-3, B60-B61.
Malinowski et al., Rocz. Chem 48, pp. 359-360 (1974), "Dimerization & Oligomerization".

*Primary Examiner*—Delbert E. Gantz
*Assistant Examiner*—G. E. Schmitkons

[57] ABSTRACT

Method for the conversion of butadiene (1,3) comprising contacting butadiene (1,3) with zinc iodide, zinc bromide (or mixtures thereof) and a reactant selected from methanol, dimethyl ether, or mixtures thereof, at a temperature of from about 180° C to about 450° C.

15 Claims, No Drawings

CONVERSION OF BUTADIENE (1,3) AND METHANOL

BACKGROUND OF THE INVENTION

This invention relates to the conversion of butadiene (1,3). In its preferred form, the invention provides a novel process for the production of higher molecular weight hydrocarbons, such as isopentane, triptane, benzene, ethyl benzene, toluene, etc., utilizing a feedstock of butadiene (1,3) and methanol.

SUMMARY OF THE INVENTION

Accordingly, the invention comprises a process in which butadiene (1,3) is reacted or contacted with methanol and a material selected from zinc iodide, zinc bromide, or mixtures thereof, at a temperature of from 180° C. to 450° C. The products of the reaction include a significant proportion of aromatic hydrocarbons, and the reaction products may be treated by conventional techniques. In its preferred form, the invention comprises a process in which butadiene (1,3) is contacted with methanol and a material selected from zinc iodide, zinc bromide, and mixtures thereof, at a temperature of from 190° C. to 350° C., and most preferably from 200° C. to 280° C.

DETAILED DESCRIPTION OF THE INVENTION

The source of butadiene (1,3) is a matter of choice. The butadiene (1,3) need not be pure, provided the impurities or dilutants (or their reaction products) do not interfere significantly with the conversion. Thus, other diolefins, olefins, and alkanes, all of which are commonly present in refinery or petrochemical streams, may be present. However, olefins, as noted in our co-pending U.S. application Ser. No. 850,872 entitled Process for Methylation of Olefins, filed even date herewith, give a different product mix with methanol, possibly necessitating additional separation techniques. It is an advantage of the invention that such streams may be employed and their contents upgraded to higher value products.

The use of methanol, at least in higher mol ratios vis-a-vis butadiene (1,3), generally results in a different product mix, e.g., a greater proportion of hexamethylbenzene, than that process disclosed in U.S. copending application Ser. No. 850,875 of T. E. Paxson and M. M. Wald entitled Butadiene (1,3) Conversion, filed even date herewith.

The source of the methanol employed is a matter of choice. For example, methanol derived from synthesis gas produced from coal, and methanol produced from natural gas are eminently suited to the practice of the invention. The purity of the methanol is not critical, provided the impurities do not interfere with the reaction. Thus, small amounts of water and ethanol, common impurities in methanol, do not interfere. Similarly, the presence of small amounts of synthesis gas from a synthesis gas conversion system does not interfere substantially with the methanol conversion reaction. The degree of purity of the methanol employed will, of course, affect the quantity of products, when considered with respect to total volume of feed material to the reactor, but the decision to use greater purity methanol must be viewed in the light of the increased cost of purification of the methanol prior to use. In general, dilute streams of methanol may be used, provided, as noted, the diluents do not interfere with the activity of the zinc iodide or zinc bromide. The term "methanol", as used in the specification and claims, is intended to include the use of such dilute streams containing methyl alcohol. Moreover, any material which will react to provide methanol in situ under the reaction conditions specified herein, and which does not interfere with the conversion reaction, and whose other reaction product or products, if any, do not interfere with the reaction is within the scope of the invention. For example, since dimethyl ether decomposes under the reaction conditions employed to form methanol, dimethyl ether may be used as a source of methanol, either as the total feed, or a portion thereof. Under some conditions, disclosed herein, significant quantities of dimethyl ether may be formed. This dimethyl ether may be separated and recycled, thereby providing a highly efficient use of source materials.

In the same manner, the zinc iodide or zinc bromide need not be pure, but may contain impurities which do not interfere with the reaction. Commercial grade zinc iodide and zinc bromide are acceptable in the process of the invention, and mixtures of zinc bromide and zinc iodide may be used.

The temperatures employed in the reaction are significant. In general, the reaction of butadiene (1,3) and methanol is suitably carried out at temperatures of from about 180° C. to about 450° C., preferably about 190° C. to about 350° C., and most preferably from about 200° C. to about 280° C. The reaction produces, at lower butadiene (1,3) ratios and below about 250° C., a significant proportion of triptane, as well as aromatic hydrocarbons. At higher butadiene (1,3) ratios, and temperatures above about 250° C., cyclodimerization occurs in greater amounts, and significant proportions of aromatic compounds are produced. Accordingly, aromatization of the butadiene (1,3) occurs in greater amounts in the presence of methanol at temperatures of from about 250° C. to about 450° C., and the preferred temperatures are from about 325° C. to about 400° C.

Pressures employed in the reaction zone are not critical, and may vary widely. Thus, pressures may be atmospheric, below atmospheric, or greater than atmospheric. As a practical matter, pressure in a batch-type system may be atmospheric initially, but will rise as temperatures are raised. Pressures on the order of 2000 psig or even higher may be used, and the selection of the appropriate pressure to be employed is well within the skill of the art.

The ratio of methanol to butadiene (1,3) is widely variable, and those skilled in the art may vary the proportions as desired. Thus, a ratio of from about 0.2 mols to 25 mols of methanol per mol of butadiene (1,3) may be employed, with a ratio of from 0.5 mols to 10 mols of methanol to butadiene (1,3) being preferred. At the same time, however, the reaction of butadiene (1,3) and methanol requires that an effective amount of zinc iodide, zinc bromide, or their mixture, i.e., an amount sufficient to initiate and sustain the reaction, be present. Again, those skilled in the art may readily determine appropriate amounts, keeping in mind that excessively high ratios of methanol to $ZnI_2$, $ZnBr_2$, or their mixture may not be used. For example, ratios of from about 0.01 mol of methanol per mol of $ZnI_2$, etc. to about 24 mols of methanol per mol of $ZnI_2$, etc. may be used, while ratios of from about 0.1 mol of methanol per mol of $ZnI_2$, etc. to about 10 mols of methanol per mol of $ZnI_2$, etc. are preferred. In the case of mixtures of $ZnI_2$ and ZnBr$_2$, the ratios of mols of "mixture" to methanol are similar, the number of mols of "mixture" being the sum of the number of mols of each component. Where dimethyl ether is used as a feed, the ratio of feed to ZnI$_2$ or ZnBr$_2$ would be similar, and where dimethyl ether is used as a portion of the feed, adjustment of the feed ratio may be made readily.

The process may be conducted batch-wise or in a continuous fashion. Whichever procedure is employed, good mixing or contact of the ZnI$_2$, ZnBr$_2$, or their mixture and methanol and butadiene (1,3) is important for good results. Any reaction system which provides a high degree of mixing or contact of reactants may be employed. For example, fixed bed systems, slurry reactors, and trickle bed reactors may be used. Contact times are not critical, and those skilled in the art may vary the contact times to provide sufficient contact time to produce optimum results, depending on, e.g., volume of reactants, reactor design, temperature, etc. For example, utilizing a fixed bed reactor design, and continuous flow of reactants, contact times on the order of from about 0.5 minute (245° C.) to about 120 minutes, or 180 minutes (200° C.), or even longer, may be used. Where batch procedures are employed, contact times may be considerably longer. In both batch and continuous procedures, it is not necessary that 100 percent conversion of the reactants be obtained before recovering the product. The products may be separated before use, or the reaction products mixture may be used as is for desired purposes.

DETAILED DESCRIPTION OF THE INVENTION

In order to describe the invention with greater particularity, reference is made to the following examples.

EXAMPLE 1

A 300-ml, Hastelloy B autoclave was charged with 200 gms (626 mmol) of ZnI$_2$. The autoclave reactor was sealed and pressure tested with N$_2$ gas. Butadiene (1,3) 11.2 gms (207 mmol) was measured out and added to 11.2 gms (350 mmol) of methanol in a Jerguson vessel which was pressured to 300 psig with N$_2$. The reactor was preheated to 200° C. and the methanol/butadiene mixture pumped into the hot ZnI$_2$ over a 16 minute period. The reactor was maintained at 200° C. an additional hour.

From the reactor was isolated 5.4 gms of organic material and 9.5 gms of an aqueous solution. Analysis of the organic layer revealed the following composition:

| Compound | Weight % |
|---|---|
| i-C$_4$H$_{10}$ | 4.8 |
| 1,3-C$_4$H$_6$ | 1.4 |
| i-C$_5$H$_{12}$ | 11.0 |
| C$_6$ hydrocarbons | 10.3 |
| C$_7$ (triptane) | 11.4 |
| other C$_7$/C$_8$ hydrocarbons | 13.0 |
| C$_9$/C$_{12}$ hydrocarbons | 28.1 |
| Me$_6$C$_6$ (hexamethyl benzene) | 14.3 |

-continued

| Compound | Weight % |
|---|---|
| | 94.3 |

EXAMPLE 2

Example 1 was repeated, except that the ratio of methanol to butadiene (1,3) was changed. The relative amounts of triptane make (representative aliphatic) to hexamethylbenzene make (aromatic) are compared in the table below:

| Reactants | | | Products | | | |
|---|---|---|---|---|---|---|
| methanol gms (mmol) | Butadiene gms (mmol) | molar ratio | organic (gms) | aqueous (gms) | parts triptane (aliphatic) | hexamethylbenzene (aromatic) |
| 17.4 (543) | 9.7 (179) | 3:1 | 6.3 | 12.4 | 50.7 | 1.5 |
| 13.3 (415) | 11.2 (207) | 2:1 | 5.4 | 9.5 | 9.1 | 10.9 |
| 3.6 (112) | 12.3 (227) | 1:2 | 3.1 | 3.0 | 19.3 | 19.7 |

What we claim is:

1. A method comprising contacting butadiene (1,3) with a material selected from the group consisting of methanol; dimethyl ether; other materials which react to provide methanol in situ, other reaction products, if any, being non-interfering; and mixtures thereof, and with an effective amount of a metal halide selected from ZnI$_2$, ZnBr$_2$, and mixtures thereof at a temperature of from 180° C. to about 450° C.

2. The method of claim 1 wherein the temperature is from about 190° C. to about 350° C.

3. The method of claim 2 wherein the metal halide is ZnI$_2$.

4. The method of claim 2 wherein the metal halide is ZnBr$_2$.

5. The method of claim 2 wherein the metal halide is a mixture of ZnI$_2$ and ZnBr$_2$.

6. A method comprising contacting butadiene (1,3) with methanol and with an effective amount of a metal halide selected from ZnI$_2$, ZnBr$_2$, and mixtures thereof at a temperature of from about 180° C. to about 450° C.

7. The method of claim 6 wherein the temperature is from about 190° C. to about 350° C.

8. The method of claim 7 wherein the metal halide is ZnI$_2$.

9. The method of claim 7 wherein the metal halide is ZnBr$_2$.

10. The method of claim 7 wherein the metal halide is a mixture of ZnI$_2$ and ZnBr$_2$.

11. A method comprising contacting butadiene (1,3) with dimethyl ether and with an effective amount of a metal halide selected from ZnI$_2$, ZnBr$_2$, and mixtures thereof at a temperature of from about 180° C. to about 450° C.

12. The method of claim 11 wherein the temperature is from about 190° C. to about 350° C.

13. The method of claim 12 wherein the metal halide is ZnI$_2$.

14. The method of claim 12 wherein the metal halide is ZnBr$_2$.

15. The method of claim 12 wherein the metal halide is a mixture of ZnI$_2$ and ZnBr$_2$.

* * * * *